(12) United States Patent
Dezawa

(10) Patent No.: US 9,441,199 B2
(45) Date of Patent: Sep. 13, 2016

(54) CELLS EXHIBITING NEURONAL PROGENITOR CELL CHARACTERISTICS AND METHODS OF MAKING THEM

(71) Applicant: SanBio, Inc., Mountain View, CA (US)

(72) Inventor: Mari Dezawa, Kyoto (JP)

(73) Assignee: SanBio, Inc., Mountain View, CA (US)

( * ) Notice: Subject to any disclaimer, the term of this patent is extended or adjusted under 35 U.S.C. 154(b) by 0 days.

(21) Appl. No.: 14/735,005

(22) Filed: Jun. 9, 2015

(65) Prior Publication Data

US 2015/0267169 A1 Sep. 24, 2015

Related U.S. Application Data

(63) Continuation of application No. 13/672,341, filed on Nov. 8, 2012, now abandoned, which is a continuation of application No. 13/068,888, filed on May 23, 2011, now abandoned, which is a continuation of application No. 11/100,664, filed on Apr. 7, 2005, now abandoned.

(60) Provisional application No. 60/561,613, filed on Apr. 12, 2004.

(51) Int. Cl.
| | |
|---|---|
| *A61K 35/12* | (2015.01) |
| *A61K 35/28* | (2015.01) |
| *C12N 5/079* | (2010.01) |
| *C12N 5/0793* | (2010.01) |
| *C12N 5/0775* | (2010.01) |
| *A61K 35/30* | (2015.01) |

(52) U.S. Cl.
CPC ............ *C12N 5/0619* (2013.01); *A61K 35/12* (2013.01); *C12N 2501/01* (2013.01); *C12N 2501/115* (2013.01); *C12N 2501/13* (2013.01); *C12N 2501/155* (2013.01); *C12N 2501/415* (2013.01); *C12N 2501/60* (2013.01); *C12N 2501/70* (2013.01); *C12N 2501/727* (2013.01); *C12N 2506/1353* (2013.01)

(58) Field of Classification Search
CPC ............ A61K 35/12; C12N 2501/155; C12N 2501/01; C12N 2501/13; C12N 5/0619; C12N 2501/60; C12N 2501/415; C12N 2501/727; C12N 2506/1353; C12N 2501/115; C12N 2501/70
See application file for complete search history.

(56) References Cited

U.S. PATENT DOCUMENTS

| | | | |
|---|---|---|---|
| 6,080,747 | A | 6/2000 | Uckun et al. |
| 6,080,748 | A | 6/2000 | Uckun et al. |
| 7,015,037 | B1 | 3/2006 | Furcht et al. |
| 7,229,827 | B2 | 6/2007 | Kim et al. |
| 2001/0044122 | A1 | 11/2001 | Buck et al. |
| 2002/0012903 | A1 | 1/2002 | Goldman et al. |
| 2003/0003090 | A1 | 1/2003 | Prockop et al. |
| 2004/0052762 | A1 | 3/2004 | Yu et al. |
| 2004/0062753 | A1 | 4/2004 | Rezania et al. |
| 2004/0209799 | A1* | 10/2004 | Vasios ............... A61K 31/00 514/1 |

FOREIGN PATENT DOCUMENTS

| | | |
|---|---|---|
| EP | 1479767 | 11/2004 |
| WO | WO 99/43286 | 9/1999 |
| WO | WO 99/56759 | 11/1999 |
| WO | WO 03/014317 | 2/2003 |
| WO | WO 03/066856 | 8/2003 |

OTHER PUBLICATIONS

Koloenko et al. (1999) Blood 93(7) 2308-2318.*
Akerud, et al., "Differential Effects of Glial Cell Line-Derived Neurotropidc Factor and Neurturin on Developing and Adult Substantia Nigra Dopaminergic Neurons," Journal of Neurochemistry 73(1):70-78 (1999).
Alberts, et al., "Molecular Biology of the Cell," Chapter 23 entitled Specialized Tissues, Stem Cells, and Tissue Renewal, fifth edition, Garland Science, New York, NY, (2008).
Bishop, et al. "Embryonic Stem Cells," Journal of Pathology 197:424-429 (2002).
Burdon, et al. "Signalling, Cell Cycle and Pluripotency in Embryonic Stem Cells," Trends Cell Biol. 12:432-438 (2002).
Cacalano et al., From The Jak-Stat Pathway in Hematopolesis and Disease, pp. 1-3, accessed online at http://www.landesbioscience.com/curie/chapter/66/ on Dec. 5. 2013.
Castro, et al., "Response to Comment on Failure of Bone Marrow Cells to Transdifferentiate Into Neural Cells in Vivo." Science 299:1184c (2003).
Dezawa et al., "Transdifferentiation of Bone Marrow Stromal Cells to Neural Cells and Application to Stem Cell Therapy," Acta Anatomica Nipponica 78suppl:97 (Abstract S04-6) (2003) (English translation also enclosed).
Dezawa, et al, "Sciatic Nerve Regeneration in Rats Induced by Transplantation of in Vitro Differentiated Bone-Marrow Stromal Cells," The European Journal of Neuroscience 14(11):1771-1776 (2001).
Dezawa, et al., "Specific Induction of Neuronal Cells From Bone Marrow Stromal Cells and Application for Autologous Transplantation," J Clin Invest 113(2):1701-1710 (2004).
Dezawa, et al., "Treatment of Neurodegenerative Diseases Using Adult Bone Marrow Stromal Cell-Derived Neurons," Expert Opinion on Biological Therapy 5(4):427-435 (2005).
Eglitis, et al. "Targeting of Marrow-Derived Astrocytes to the Ischemic Brain," Neurareport 10(6):1289-1292 (1999).
EMD, accessed at http://www.emdchemicals.com/life-science-researchlstat-signalinginhibitors/c_QOib.slOq3YAAAEjKxx9.zLX on Feb. 15, 2012, pp. 1-4.

(Continued)

*Primary Examiner* — Thaian N Ton
(74) *Attorney, Agent, or Firm* — Levine Bagade Han LLP

(57) ABSTRACT

Disclosed are cells exhibiting neuronal progenitor cell characteristics, and methods of making them from marrow adherent stem cells by regulating cellular pathways in the marrow adherent stem cells that are associated with glial transdifferentiation of the marrow adherent stem cells.

15 Claims, No Drawings

(56) References Cited

OTHER PUBLICATIONS

Franklin, et al. "Autonomous and Non-Autonomous Regulation of Mammalian Neurite Development by Notch! and Deltai," Current Biology 2:1448-1457 (1999).

Furukawa, et al. "RAX, HESI, and Notchi Promote the Formation of Muller Glia by Postnatal Retinal Progenitor Cells," Neuron 212:383-394 (2000).

Gaiano, et al. "Radial Glial Identity is Promoted by Notchi Signaling in the Murine Forebrain," Neuron 26 (2): 395-404 (2000).

Giavaski-Loksimovic, et al., "Reversal of Dopaminergic Degeneration in a Parkinsonian Rat Following Micrografting of Human Bone Marrow-Derived Neural Progenitors," Cell Transplantation 18:801-814 (2009).

Gobbel, et al., "Cellular Transplantation for the Nervous System; Impact of Time After Preparation on Cell Viability and Survival," J. of Neurosurg 113:666-672 (2010).

Gratsch, et al., "Noggin and Chordin Induce Neural Gene Expression in Bone Marrow Stromal Cells," Society for Neuroscience Abstracts vol. 27(1 ):52 (2001).

Gregg, et al., "Radial Glial Cells as Neuronal Precursors: The Next Generation?" Journal of Neuroscience 69:708-713 (2002).

Gregory et al., Experimental Cell Res., 306: 330-335,2005.

Grosse, et al., "Expression of KVI Potassium Channels in Mouse Hippocampal Primary Cultures: Development and Activity-Dependent Regulation," The Journal of Neuroscience 20(5):1869-1882 (2000).

Hofstetter, et al., "Marrow Stromal Cells for Guiding Strands in the Injured Spinal Cord and Promote Recovery," PNAS 99:2199-2204 (2002).

Huttmann, et al., "Bone Marrow-Derived Stem Cells and "Plasticity"," Ann Hematol 82:599-604 (2003).

Ip, "The Neurotrophins and Neuropoietic Cytokines: Two Families of Growth Factors Acting on Neural and Hematopoietic Cells," Annals New York Academy of Sciences 840: 97-106 (1998).

Ishibashi, et al. "Persistent Expression of Helix-Loop-Helix Factor HES-I Prevents Mammalian Neural Differentiation in the Central Nervous System," EMBO J. 13(8):1799-1805 (1994).

Jiang, et al., "Pluripotency of Mesenchymal Stem Cells Derived From Adult Marrow," Nature 418:41-49 (2002).

Kabos, et al., "Blocking HESI Expression Inititaes Gabaergic Differentiation and Induces the Expression of P21 CIP1IWAFI in Human Neural Stem Cells," J. Biol Chem 11:8763-8766 (2002).

Kahn, et al., "Ciliary Neurotrophic Factor Activates Jakistat Signal Transduction Cascade and Induces Transcriptional Expression of Glial Fibrillary Acidic Protein in Glial Cells," Journal of Neurochemistry 68(4):1413-1423 (1997).

Kawasaki, et al. ,"Induction of Midbrain Dopaminergic Neurons From ES Cells by Stromal Cell-Derived Inducing Activity," Neuron 28(1):31-40 (2000).

Kim, et al., "Creating Permissive Microenvironments for Stem Cell Transplantation into the Central Nervous System," Trends in Biotechnology 30:55-63 (2012).

Kim, et al., "Dopamine Neurons Derived From Embryonic Stem Cells Function in an Animal Model of Parkinson's Disease," Nature 418:50-56 (2002).

Kohyama, et al., "Brain From Bone: Efficient "Meta-Differentiation" of Marrow Stromaderived Mature Osteoblasts to Neurons With Noggin or a Demethylating Agent," Differentiation 68:235-244 (2001).

Kopen, et al., "Marrow Stromal Cells Migrate Throughout Forebrain and Cerebellum, and They Differentiate into Astrocytes After Injection Into Neonatal Mouse Brains," PNAS 96:10711-10716 (1999).

Kurooka, et al.,"Roles of the Ankyrin Repeats and C-Terminal Region of the Mouse Notchi Intracellular Region," Nucleic Acids Research 26(23):5448-5455 (1998).

Lendahl, et al., "CNS Stem Cells Express a New Class of Intermediate Filament Protein," Cell 60:585-595 (1990).

Liker, at al., "Human Neural Stem Cell Transplantation in the MPTP-Lesioned Mouse," Brain Research 971:168-177 (2003).

Lonza web page, Poietics® hMSC Human Mesenchymal Stem Cells & Media.

Lu, et al., "Induction of Bone Marrow Stromal Cells to Neurons: Differentiation, Transd ifferentia tion, or Artifact?" Journal of Neuroscience Research 77:174-191 (2004).

Lu, at al., "Intraarterial Administration of Marrow Stromal Cells in a Rat Model of Traumatic Brain Injury," J. Neurotrauma 18:813-819 (2001).

Lundkvist, et al., "Notch and the Birth of Glial Cells," Trends in Neuroscience 24(9):492-494 (2001).

Luo, at al., "Inhibitors of JAKS/STATS and the Kinases: A Possible New Cluster of Drugs," Drug Discovery Today 9:268-275 (2004).

Majumdar et al., J. of Hematotheraphy & Stem Cell Research, 9: 841-848, 2000.

Medline Plus (http://www.nhn.nih.gov/medlineplus/peripheral-nervedisorders.html, accessed online on Feb. 14, 2012).

Morrison, et al., "Neuronal Differentiation: Proneural Genes Inhibit Gliogenesis," Current Biology 11(9):R349-R351 (2001).

Morrison, et al., "Transient Notch Activation Initiates an Irreversible Switch From Neurogenesis to Gliogenesis by Neural Crest Stem Cells," Cell 101:499-510 (2000).

Nakashima, et al., "BMP2-Mediated Alteration in the Developmental Patiiway of Fetal Mouse Brain Cells From Neurogenesis to Astrocytogenesis," PNAS 98(10):5868-5873 (2001).

Neububer, et al., "Reevaluation of in Vitro Differentiation Protocols for Bone Marrow Stromal Cells: Disruption of Actin Cytoskeleton Induces Rapid Morphological Changes and Mimics Neuronal Phenotype," Journal of Neuroscience Research 77:192-204 (2004).

Neufeld, et al., "Serineithreonine Kinases 3PK and MAPK-Activated Protein Kinase 2 Interact with the Basic Helix-Loop-Helix Transcription Factor E47 and Repress Its Transcriptional Activity," The Journal of Biological Chemistry 275(27):20239-20242 (2000).

Nye, et al., "An Activated Notch Suppresses Neurogenesis and Myogenesis but not Gliogenesis in Mammalian Cells," Development 120(9):2421-2430 (1994).

Peyton, et al. "BETA3, A Novel Helix-Loop-Helix Protein, Can Act as a Negative Regulator of BETA2 and MYOD-Responsive Genes," Molecular and Cellular Biology .16(2):626-633 (1996).

Pittenger, et al., "Multilineage Potential of Adult Human Mesenchymal Stem Cells," Science 284:143-147 (1999).

Qian, et al., "Improving the Expansion and Neuronal Differentiation of Mesenchymal Stem Cells Through Culture Surface Modification," Biomaterials 25:1331-1337 (2004).

Rawlings, et al., "The JAK/STAT Signaling Pathway," Journal of Cell Science 117:1281-1283 (2004).

Roche (http://www.roche.com/research_anddevelopment/r_d_overview/pharmaceuticals/r_d_central_nervous_system.htm, accessed online on Feb. 14, 2012.

Rotondo, et al, "MAP-2 Expression in the Human Adenohypophysis and in Pituitary Adenomas an Immunohistochemical Study," Pituitary 8:75-79 (2005).

Roy, et al., "In Vitro Neurogenesis by Progenitor Cells Isolated From the Adult Human Hippocampus," Nature Medicine 6(3)271-277 (2000).

Rozovsky, et al., "Estradiol (E2) Enhances Neurite Outgrowth by Repressing Glial Fibrillary Acidic Protein Expression and Reorganizing Laminin," Endocrinology 143(2):636-646 (2002).

Sakurada, et al., "NURR1, An Orphan Nuclear Receptor, is a Transcriptional Activator of Endogenous Tyrosine Hydroxylase in Neural Progenitor Cells Derived From the Adult Brain," Development 126:4017-4026 (1999).

Sanchez-Ramos, "Neural Cells Derived From Adult Bone Marrow and Umbilical Cord Blood:" Journal of Neuroscience Research 69:880-893 (2002).

Schwaiger, et al., "Peripheral but not Central Axotomy Induces Changes in Janus Kinases (JAK) and Signal Transducers and Activators of Transcription (STAT)," European Journal of Neuroscience 12:1165-1176 (2000).

Seidel, et al., "Pharmaceutical Intervention in the JAKJSTAT Signaling Pathway," Oncogene 19:2645-2656 (2000).

Seta, et al., "Expression of Mash1 in Basal Cell of Rat Circumvallate Taste Buds is Dependent Upon Gustatory Innervation," FEBS Lett. 444:43-46 (1999).

(56) References Cited

OTHER PUBLICATIONS

Shibata, et al., "Glutamate Transporter Glast is Expressed in the Radial Glia-Astrocyte Lineage of Developing Mouse Spinal Cord," The Journal of Neuroscience 17(23): 9212-9219 (1997).

Shimazaki, et al., "The Ciliary Neurotrophic Factor/Leukemia Inhibitory Factor/GP130 Receptor Complex Operates in the Maintenance of Mammalian Forebrain Neural Stem Cells," The Journal of Neuroscience 21(19): 7642-7653 (2001).

Siegel, et al., The Basic Neurochemistry, 6th Edition, 1999, accessed online at http:/www.ncbi.nih.gov/booksfNBK28209/ on Feb. 16, 2012, pp. 1-12.

Song, et al., "Neural Stem Cells From Adult Hippocampus Develop Essential Properties of Functional CNS Neurons," Nat. Neuroscience 5:438-445 (2002).

Stork, et al., "Crosstalk Between Camp and Map Kinase Signaling in the Regulation of Cell Proliferation," Trends in Cell Biology 6(12):258-266 (2002).

Sudbeck, et al., "Structure-Based Design of Specific Inhibitors of Janus Kinase 3 as ApoptosisInducing Antileukemic Agents," Clinical Cancer Research 5:1569-1582 (1999).

Sun, et al., "Neurogenin Promotes Neurogenesis and Inhibits Glial Differentiation by Independent Mechanisms," Cell 104:365-376 (2001).

Tanaka, et al., "Role of Serotonergic Neurons in L-DOPA-Derived Extracellular Dopamine in the Striatum of 6-0HDA-Lesioned Rats," NeuroReport 10:631-634 (1999).

Terada, et al., "Bone Marrow Cells Adopt the Phenotype of Other Cells by Spontaneous Cell Fusion," Nature 416:542-545 (2002).

Turnley, et al., "Cytokines That Signal Through the Leukemia Inhibitory Factor Receptorbeta Complex in the Nervous System," Journal of Neurochemistry 74(3):889-899 (2000).

Uckun et al., Clin. Cancer Research, 5: 2954-2962, 1999.

Vieyra, et al,. "Plasticity and Tissue Regernative Potential of Bone Marrow-Derived Cells," Stem Cell Reviews 1:65-70 (2005).

Vogel, et al., "Heterogeneity Among Human Bone Marrow-Derived Mesenchymal Stem Cells and Neural Progenitor Cells," Haematologica/journal of hematology 88:126-133 (2003).

Wagers, et al., "Little Evidence for Developmental Plasticity of Adult Hematopoietic Stem Cells." Science 297:2256-2259 (2002).

Weinmaster, et al., "A Homolog of *Drosophila* Notch Expressed during Mammalian Development," Development 113:199-205 (1991).

Weissman, "Stemcells: Units of Development, Units of Regneration and Units in Evolution," Cell 100:157-168 (2000).

Woodbury, et al., "Adult Bone Marrow Stromal Stem Cells Express Germline, Ectodermal, Endodermal, and Mesodermal Genes Prior to Neurogenesis," J Neuroscience Research 96:908-917 (2002).

Woodbury, et al., "Adult Rat and Human Bone Marrow Stromal Cells Differentiate Into Neurons," Journal of Neuroscience Research 61:364-370 (2000).

Wright, et al., "Gene Expression in Human Neural Stem Cells: Effects of Leukemia Inhibitory Factor," Journal of Neurochemistry 86:179-195 (2003).

Xu, et al., "Enhancing CNS Repair in Neurological Disease: Challenges Arising From Neurodegeneration and Rewiring of the Network," CNS Drugs 25:555-573 (2011).

Yamaguchi, et al., "Visualization of Neurogenesis in the Central Nervous System Using Nestin Promoter-GFP Transgenic Mice," NeuroReport 11:1991-1996 (2000).

Yamamoto, et al. "Role of Deltex-I as a Transcriptional Regulator Downstream of the Notch Receptor.," J Biol .Chern 276(48):45031-45040 (2001).

Yamasaki, et al., "3-Phosphoglycerate Dehydrogenase, A Key Enzyme for L-Serine Biosynthesis, is Preferentially Expressed in the Radial Glia/Astrocyte Lineage and Olfactory Ensheathing Glia in the Mouse Brain" The Journal of Neuroscience 21(19)):7691-7704 (2001).

Yasuhara, et al., "Stem Notch-Induced Rat and Human Bone Marrow Stromal Cell Grafts Reduce Ischemic Cell Loss and Ameliorate Behavioral Deficits in Chronic Stroke Animals," Cells and Development 18:1501-1513 (2009).

Cutler et al., "Dude, where's my phenotype? Dealing with redundancy in signaling networks," *Plant Physiology*, 138:558-559, 2005.

Ge et al., "Notch signaling promotes astrogliogenesis via direct CSL-mediated glial gene activation," *Journal of Neuroscience Research*, 69:848-860, 2002.

Josten et al., "Cooperation of JAK/STAT and Notch signaling in a *Drosophila* foregut," *Developmental Biology*, 267:181-189, Mar. 2004.

Kiger et al., "Stem cell self-renewal specified by JAK-STAT activation in response to a support cell cue," *Science*, 294:2542-2545, 2001.

Sanchez-Ramos, "Adult bone marrow stromal cells differentiate into neural cells in vitro," *Experimental Neurology*, 164:247-256, 2000.

Ivanova, Natalia B. et al., "A Stem Cell Molecular Signature," Science, 298:601-604, Oct. 18, 2002.

* cited by examiner

CELLS EXHIBITING NEURONAL PROGENITOR CELL CHARACTERISTICS AND METHODS OF MAKING THEM

CROSS-REFERENCE TO RELATED APPLICATIONS

This application is a continuation of U.S. patent application Ser. No. 13/672,341 filed Nov. 8, 2012, which is a continuation of U.S. patent application Ser. No. 13/068,888 filed May 23, 2011, which is a continuation of U.S. patent application Ser. No. 11/100,664 filed Apr. 7, 2005 which claims priority to U.S. Provisional Patent Application 60/561,613 filed Apr. 12, 2004, the contents of which are incorporated herein by reference in their entirety.

FIELD OF THE INVENTION

The invention relates to cells exhibiting neuronal progenitor cell characteristics, and methods of making them from marrow adherent stem cells by regulating cellular pathways in the marrow adherent stem cells that are associated with glial transdifferentiation of the marrow adherent stem cells.

BACKGROUND OF THE INVENTION

A limitation in the research and treatment of Central Nervous System (CNS) or Peripheral Nervous System (PNS) diseases is the conventional recognition that terminally differentiated neurons are significantly limited in their ability to proliferate. Accordingly, any treatment of CNS or PNS diseases that requires transplant of terminally differentiated neurons is difficult to accomplish.

One proposed approach to overcoming this difficulty has been to culture large numbers of mitotic cells exhibiting neuronal progenitor cell characteristics ("CPCs"). Such cells could theoretically differentiate in vivo into neurons that could function in the treatment of CNS and/or PNS diseases. Alternatively, CPCs might be differentiated in vitro into neurons and then transplanted into patients. However, such CPCs are rare and difficult to isolate from donors. Therefore, conventionally, researchers have attempted to obtain CPCs from treated embryonic and fetal stem cells (collectively referred to as "embryonic stem cells" hereinafter).

Embryonic stem cells, which are pluripotent cells, have been used to generate a large variety of tissue types, and could be a source of CPCs. I. Weissman, *Stem cells: units of development, units of regeneration, and units in evolution (Review)*. Cell 100, 157-168 (2000). However, the use of embryonic stem cells raises a number of ethical concerns, and so is a disfavored source of stem cells for production of CPCs. Additionally, embryonic stem cells can be tumorigenic, which generates safety concerns as to any transplant procedure that could potentially result in the delivery of embryonic stem cells to a patient such as creation of a CPC graft from embryonic stem cells.

Some researchers have attempted to utilize other types of stem cells, such as mesenchymal stem cells in the production of CPCs. U.S. Patent Application 20030003090 of Prockop, et al., filed Jan. 2, 2003, and entitled "Directed in vitro differentiation of marrow stromal cells into neural cell progenitors" discloses that the expression levels of both NSE and vimentin were increased in human mesenchymal stem cells after their incubation with 0.5 millimolar IBMX and 1 millimolar dbcAMP. The increase in NSE and vimentin mRNAs coincided with the appearance of neural cells in the cultures. However, Prockop et al. reported that there was no change in the expression level of either MAP1 B or TuJ-1. Since NSE, MAP1 B, and TuJ-1 are early neuron-characteristic markers, and vimentin is an early marker for glia, Prockop et al. suggested that the hMSCs transdifferentiated in vitro into some early progenitors of either neurons or glia. However, the early progenitor cells of Prockop may be undesirable for use because they seem to display a very immature neuronal phenotype whose clinical efficacy is not well understood.

Accordingly, there is a scarcity of conventionally available and suitable sources of CPCs for use, for example, in the research and treatment of CNS or PNS diseases. Further, there is a scarcity of methods that can be used to produce such CPCs in a suitable manner suitable for use. What are needed are methods and compositions that overcome such problems.

SUMMARY OF THE INVENTION

In an aspect, the invention relates to a method of producing cells exhibiting neuronal progenitor cell characteristics from material comprising marrow adherent stem cells, the method comprising: regulating cellular pathways in the marrow adherent stem cells that are associated with glial transdifferentiation of the marrow adherent stem cells; wherein the cellular pathways are sufficiently regulated to induce at least a portion of the marrow adherent stem cells to transdifferentiate into cells exhibiting neuronal progenitor cell characteristics; and with the proviso that the regulating does not comprise transfection of the marrow adherent stem cells with notch intracellular domain.

In another aspect, the invention relates to a method for producing cells exhibiting neuronal progenitor cell characteristics comprising: incubating marrow adherent stem cells with a glial regulating agent in an amount sufficient to induce at least a portion of the marrow adherent stem cells to transdifferentiate into cells exhibiting neuronal progenitor cell characteristics; with the proviso that the interacting does not comprise transfection of the marrow adherent stem cells with notch intracellular domain.

DETAILED DESCRIPTION OF THE INVENTION

The inventor has unexpectedly and surprisingly discovered that the problems and limitations noted above can be overcome by practicing the invention disclosed herein. The present invention addresses producing CPCs from marrow adherent stem cells (MASCs) by regulating cellular pathways in MASCs that are associated with glial transdifferentiation of the MASCs. Ways to make and use the invention are disclosed herein.

All references cited herein are incorporated herein by reference in their entirety and for all purposes to the same extent as if each individual publication or patent or patent application was specifically and individually indicated to be incorporated by reference in its entirety for all purposes. The discussion of references herein is intended merely to summarize the assertions made by their authors and no admission is made that any reference constitutes prior art. Applicants reserve the right to challenge the accuracy and pertinence of the cited references.

Cells exhibiting neuronal progenitor cell characteristics ("CPCs") are defined as, for the purposes of this invention, being cells that are mitotic, express nestin and other cell markers specific for neural precursor/neural progenitor cells, and are derived from MASCs. CPCs can differentiate into neurons, glia, and oligodendrocytes, and precursors of any of the foregoing. CPCs can be derived from MASCs according to methods disclosed herein. In an embodiment, human CPCs are EfnB2+, CD90−, and PDGF receptor beta−. These markers may be used to separate CPCs from MASCs using FACS following glial transdifferentiation of the MASCs according to the present invention. Suitable methods of handling CPCs are known conventionally, including those methods disclosed, for example, in published U.S. patent application 20020012903 to Goldman et al.

Generally, CPCs according to the invention may be produced by regulating cellular pathways in MASCs that are associated with glial transdifferentiation of the MASCs, with the cellular pathways being sufficiently regulated to induce at least a portion of the MASCs to transdifferentiate into CPCs.

A wide variety of regulating methods may be useful in the practice of this invention. These include, but are not limited to, modification of the medium and conditions in which cells are grown, if grown ex vivo; modifying the tissue environment in which the MASCs are present, if grown in vivo; or incubation of the MASCs with glial regulating agents. The precise manner of regulation does not matter for the purposes of this invention, so long as glial transdifferentiation of the MASCs is effectively regulated, thus allowing differentiation of the MASCs into CPCs. Generally, the regulation of cellular pathways in MASCs that are associated with glial transdifferentiation of the MASCs takes place under conditions that are appropriate to maintain any MASCs or CPCs in a mitotic and viable state. Such conditions are known to one of skill in the art, and may be found in, for example, M. Kallos et al., *Large-scale expansion of mammalian neural stem cells: a review*. Med Biol Eng Comput. 2003 May;41(3):271-82. Suitable conditions and techniques also can be found elsewhere in the literature both for cell culture and in vivo environments.

In preferred embodiments of the invention, regulation of the cellular pathways in MASCs that are associated with glial transdifferentiation of the MASCs may be accomplished by incubating the MASCs with glial regulating agents. In a more preferred embodiment, regulation of the cellular pathways in MASCs that are associated with glial transdifferentiation of the MASCs may be accomplished by incubating the MASCs with glial regulating agents in amounts sufficient to induce at least a portion of the MASCs to transdifferentiate into CPCs. Incubations in the context of the present invention may involve culturing MASCs in the presence of glial regulating agents with the intent that the glial regulating agents either interact with MASC cell surface receptors or are transported into the interior of the MASCs to interact with internal cellular pathways. Such transportation may be passive, such as diffusive transport, or active, such as through active transporters or a mixture of the two. In vitro incubations may be performed in a conventional manner, for instance incubating cultures of MASCs in alpha-MEM, or similar media, to which glial regulating agent(s) are added. Suitable incubation techniques may be found generally in the literature, including for example M Kallos et al., *Large-scale expansion of mammalian neural stem cells: a review*. Med Biol Eng Comput. 2003 May;41(3):271-82. Incubations may also take place in an in vivo environment, in which case glial regulating agents according to the invention may be administered either systemically or locally, and using conventional methods.

In a preferred embodiment of incubation, if the glial regulating agent is a protein or peptide, the method of incubation may be a transfection of the DNA coding for that protein or peptide into the MASCs. Transfections may be performed using commercially available transfection protocols, such as the Lipofectamine™ 2000 system available from Invitrogen, or the Effectene™ transfection system available from Qiagen, or other conventional transfection protocols. In another preferred embodiment of incubation, if the glial regulating agent is a protein or peptide, the method of incubation may be viral delivery of the glial regulating agent, using conventional viral vectors, such as Lentiviral vector systems (BLOCK-iT™ Lentiviral RNAi Expression System, Invitrogen) for stable expression and Adenoviral vector systems (BLOCK-iT™ Adenoviral RNAi Expression System, Invitrogen) for transient expression.

The incubations can take place at various times: serially, in parallel or combinations of serial and parallel incubations of the MASCs with various glial regulating agent(s).

In embodiments of the invention, there is the proviso that regulating cellular pathways in the MASCs that are associated with glial transdifferentiation of the MASCs does not comprise transfection of the MASCs with the intracellular domain of the Notch gene. In embodiments of the invention, there is the proviso that incubating the MASCs with glial regulating agents does not comprise transfection of the MASCs with the intracellular domain of the Notch gene.

Marrow adherent stem cells (MASCs) are defined as being, for the purposes of this invention, stem cells that are conventionally recognized as differentiating into several types of cells found primarily in connective tissues, including but not limited to, osteoblasts, adipocytes, chondrocytes, and myocytes: MASCs specifically exclude embryonic stem cells and fetal stem cells. MASCs may be obtained from a wide variety of animals, including but not limited to humans, and other mammals such as rats, mice, primates, pigs, cows, and sheep. MASCs may be obtained from a variety of tissues; preferred sources comprise bone marrow and cord blood. Useful sources for MASCs, and methods of obtaining them are described in Example 1 below, and elsewhere herein. In an embodiment, human MASCs useful in the practice of this invention express CD29, and CD90, but are negative for CD15, CD34, CD11b/c, CD31, CD45 and von Willebrand Factor.

In an embodiment, MASCs may be isolated from cord blood using techniques described in the literature. For instance, C. Campagnoli et al., *Identification of mesenchymal stem/progenitor cells in human first-trimester fetal blood*, liver, and bone marrow. 1: Blood. 2001 Oct. 15;98(8):2396-402 describes methods generally useful in obtaining fetal blood MASCs. In A. Erices et al., *Mesenchymal progenitor cells in human umbilical cord blood*. 1: Br J Haematol. 2000 April;109(1):235-42. , there was described methods generally useful in obtaining MASCs from cord blood. L. Hou et al., *Induction of umbilical cord blood mesenchymal stem cells into neuron-like cells in vitro*. Int J Hematol. 2003 October;78(3):256-61, describes methods generally useful in obtaining purifying, and expanding human umbilical cord blood MASCs.

Glial regulating agents are defined as being, for the purposes of this invention, substances that, among other characteristics, possess the characteristic of inhibiting transdifferentiation of MASCs into glial cells and promoting their transdifferentiation into CPCs. Glial regulating agents may act through a variety of different mechanisms to direct MASCs away from the glial fate. For instance, pro-neural basic helix-loop-helix transcription factors such as Mash 1, Math 1 and neurogenin 1 are believed to be activators of neuronal gene expression.

Proneural genes are believed to drive neuronal transdifferentiation of MASCs while inhibiting glial transdifferentiation. One mechanism by which glial transdifferentiation may be inhibited is through the regulation of STAT-mediated signal transduction. Signal transduction by STAT is believed to be triggered by phosphorylation which is believed to be catalyzed by the Janus family of tyrosine kinases (JAK). Inhibition of the JAK-STAT signal transduction therefore may regulate glial transdifferentiation pathways and promote the neuronal fate of MASCs.

Glial regulating agents according to the invention may comprise inhibitors or antagonists or agents that interfere with the signaling pathways for gliogenic factors. Glial regulating agents may also comprise agonists for neurogenesis, including neurogenic factors. Use of these agonists or factors may negatively control gliogenesis of MASCs in the practice of this invention. Glial regulating agents according to the practice of this invention may comprise conventional forms of therapeutic molecules, including but not limited to small molecules, peptides, and whole or portions of gene products.

In an embodiment, glial regulating agents according to the invention include, but are not limited to, JAK/STAT inhibitors, including inhibitors of STAT1 and STAT3. In certain embodiments, such JAK/STAT inhibitors may comprise RNAi for gene silencing of the JAK/STAT pathway, antisense oligonucleotides to down regulate the JAK/STAT pathway, or the small molecule JAK inhibitor 4-(4'-hydroxypheny)amino-6,7-dimethoxyquinazoline. Additional JAK/STAT inhibitors are disclosed in U.S. Patent Application 20040209799 of George Vasios, published Oct. 21, 2004; and U.S. Patent Application 20040052762 of Hua Yu et al., published Mar. 18, 2004, the disclosures of which are incorporated by reference herein, in their entireties, for the purposes of disclosing and describing JAK/STAT inhibitors. In an embodiment, glial regulating agents according to the invention include, but are not limited to, antagonists of BMP2 or 7 (bone morphogenic protein). Such antagonists may comprise whole or portions of gene products from genes expressing Noggin, Chordin, Follistatin, sonic hedgehog (SHH), or agonists of these genes.

In an embodiment, glial regulating agents according to the invention include, but are not limited to, Hes inhibitors, including but not limited to Hes 1 and/or Hes 5 inhibitors. In certain embodiments, such Hes inhibitors may comprise RNAi for gene silencing of Hes, or antisense oligonucleotides to down regulate Hes.

In an embodiment, glial regulating agents according to the invention include, but are not limited to, inhibitors of Id-1. See S. Tzeng et al., *Id1, Id2, and Id3 gene expression in neural cells during development*. Glia. 1998 December;24(4):372-81. In certain embodiments, such Id-1 inhibitors may comprise RNAi for gene silencing of Id-1, or antisense oligonucleotides to down regulate Id-1.

In an embodiment, glial regulating agents according to the invention include, but are not limited to, inhibitors of mammalian homologs of *Drosophila* glide/gcm (glial cells missing), including but not limited to Gcm1 (murine) or GCMB (human). See Y. Iwasaki et al., *The potential to induce glial differentiation is conserved between Drosophila and mammalian glial cells missing genes*. Development. 2003 December; 130(24):6027-35. Epub 2003 October 22; and M. Kammerer et al., *GCMB, a second human homolog of the fly glide/gcm gene*. Cytogenet Cell Genet. 1999;84(1-2):43-7.). In certain embodiments, such glide/gcm homolog inhibitors may comprise RNAi for gene silencing of glide/gcm homologs (such as Gcm1(murine) or GCMB (human)), or antisense oligonucleotides to down regulate glide/gcm homologs (such as Gcm1(murine) or GCMB (human)).

In an embodiment, glial regulating agents according to the invention include, but are not limited to, inhibitors of Sox9, which may be a transcription factor for oligodendrocyte lineage. See C. Stolt et al., *The Sox9 transcription factor determines glial fate choice in the developing spinal cord*. Genes Dev. 2003 Jul. 1;17(13):1677-89.). In certain embodiments, such Sox9 inhibitors may comprise RNAi for gene silencing of Sox9, or antisense oligonucleotides to down regulate Sox9.

In an embodiment, glial regulating agents according to the invention include, but are not limited to, inhibitors of Neurogenin3, which may be a transcription factor for gliogenesis. In certain embodiments, such Neurogenin3 inhibitors may comprise RNAi for gene silencing of Neurogenin3, or antisense oligonucleotides to down regulate Neurogenin3.

In an embodiment, glial regulating agents according to the invention include, but are not limited to, inhibitors of ciliary neurotrophic factor (CNTF). In certain embodiments, such CNTF inhibitors may comprise RNAi for gene silencing of CNTF, or antisense oligonucleotides to down regulate CNTF.

In certain embodiments, glial regulating agents may comprise whole or portions of gene products from genes expressing Wnt1, which strongly inhibits gliogenesis. See K. Tang et al., *Wnt-1 promotes neuronal differentiation and inhibits gliogenesis in P19 cells*. Biochem Biophys Res Commun. 2002 Apr. 26;293 (1):167-73. Whole or portions of gene products from genes expressing Wnt1 may be administered by transfection or other conventional methods, such as gene therapy methods including viral vectors.

In certain embodiments, glial regulating agents may comprise whole or portions of gene products from genes expressing a subset of neural basic helix-loop-helix (bHLH) factors that play instructive roles during neurogenesis or are expressed in proliferating CPCs. Such glial regulating agents may comprise whole or portions of gene products from genes expressing Neurogenin1, Mash1, Math1, Math6, or NeuroD. Whole or portions of gene products from genes expressing the subset of neural basic helix-loop-helix (bHLH) factors, including but not limited to Neurogenin1, Mash1, Math1, Math6, or NeuroD, may be administered by transfection or other conventional methods, such as gene therapy methods including viral vectors.

Additionally, glial regulating agents may be administered singly or in combination. In a preferable embodiment, if a combination of glial regulating agents is used in the practice of the invention, then glial regulating agents that act on different glial regulating pathways may be selected. This may serve to enhance the overall glial regulating effect of the glial regulating agents.

For the purposes of this invention, isolating CPCs comprises isolating CPCs from non-CPC cells in a sample, such as MASCs that have not transdifferentiated into CPCs. Such isolation may comprise a single isolation or multiple isolations. If multiple isolations are to be performed, different types or techniques of isolation may be preferably used, as such different types or techniques of isolation may enhance isolation results. A wide variety of isolation methods are useful in the practice of this invention. Examples of such isolation methods include, but are not limited to flow cytometry (aka FACS sorting), magnetic separation techniques, and visual sorting. Immunocytochemistry may also be used in instances where cell viability is not critical.

FACS sorting can be performed using conventional FACS equipment and protocols with antibodies that are specific to epitopes associated with one or more characteristics of CPCs. One such epitope may be EfnB2 in the case of human CPCs. N. Ivanova et al., *A stem cell molecular signature.* Science 298(5593):601-4 (Oct. 18, 2002). Antibodies additionally useful in the practice of the invention, although not necessarily for FACS sorting, comprise anti-CD15, anti-CD29, anti-CD34, anti-CD90, anti-CD31, anti-CD45, anti-CD11b/c, and anti-von Willebrand factor. Cell populations FACS equipment useful in the practice of this invention include, but are not limited to, a FACScalibur™ analyzer with CellQuest™ software (Becton Dickinson, Franklin Lakes, N.J.), or FACS equipment available from Guava Technologies (Hayward, Calif.).

Alternatively, isolation may be performed using magnetic separation techniques, such as the BioMag™ protocols and reagents, available in kit form from Qiagen. Immunocytochemistry may be another separation technique useful in the practice of this invention; useful Immunocytochemical methods are described in M. Dezawa et al., *Sciatic nerve regeneration in rats induced by transplantation of in vitro differentiated bone-marrow stromal cells.* Eur. J. Neurosci. 14, 1771-1776 (2001). Immunocytochemical inspections may be made under a confocal laser scanning microscope, such as the Radians 2000 (Bio-Rad, Hertfordshire, UK). Conventional visual cell sorting techniques may be used in the practice of this invention.

Neurons are defined as, for the purposes of this invention, being any of the impulse-conducting cells that constitute the brain, spinal column, and nerves, consisting of a nucleated cell body with one or more dendrites and a single axon. Biochemically, neurons are characterized by reaction with antibodies for neurofilament-M, beta3-tubulin, and TuJ-1. These reactions may be used to isolate neurons or cells exhibiting one or more characteristics of neurons using techniques such as FACS sorting. Neural cells are also characterized by secreting neurotransmitters, neurotransmitter synthetases or neurotransmitter-related proteins, for example neuropeptide Y and substance P.

Neurotrophic agents are defined as being, for the purposes of this invention, substances that, among other characteristics, possess the characteristic of causing or promoting the differentiation of CPCs into neurons or cells that exhibit one or more characteristics of neurons. Neurotrophic agents useful in the practice of this invention comprise but are not limited to basic-fibroblast growth factor (bFGF), ciliary neurotrophic factor (CNTF), and forskolin (FSK). Neurotrophic agents may be combined with the CPCs of the present invention using cell handling techniques known in the art. Preferred methods may be found generally in PCT/JP03/01260 of Dezawa et al. In a preferred embodiment, bFGF, CNTF and FSK are combined with CPCs in cell culture in amounts effective to cause or promote the differentiation of CPCs into neurons or cells that exhibit one or more characteristics of neurons.

Glial cells are defined as, for the purposes of this invention, being any of the cells that make up the network of branched cells and fibers that support the tissue of the central nervous system. Glial cells include, but are not limited to astrocytes, Schwann cells, oligodendrocytes, and microglia.

Genes are defined as, for the purposes of this invention, being a set of connected transcripts, wherein a transcript is a set of exons produced via transcription followed (optionally) by pre-mRNA splicing. Gene products are defined as, for the purposes of this invention, being proteins translated from genes. Portions of genes are defined as, for the purposes of this invention, being a subset of a gene. Portions of gene products are defined as, for the purposes of this invention, being a subset of a gene product.

Patient means an animal, typically a mammal, and more typically, a human, that is the subject of medical observation or study.

CPCs produced according to the invention may be administered to patients through a variety of methods, including but not limited to infusion through an injection cannula, needle or shunt, or by implantation within a carrier, e.g., a biodegradable capsule, but other routes of administration, are also within the scope of the invention. Inventive routes of administration comprise local and systemic routes. Local administration may preferable include administration to targeted potions of the CNS or PNS, and preferably includes intraparenchymal routes. Systemically routes of administration comprise parenteral routes, with intravenous (i.v.), or intra-arterial (such as through internal or external carotid arteries) administration being preferred routes of systemic administration. Systemic administration techniques can be adapted from techniques used to administer precursor cells generally, such as those disclosed in D Lu et al., *Intraarterial administration of marrow stromal cells in a rat model of traumatic brain injury.* J Neurotrauma. 2001 August;18(8): 813-9.

Amounts of CPCs administered to a patient may be determined clinically, using conventional dose ranging techniques, and clinical assessments of a particular patient's disease.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods within the scope of the invention, in addition to those enumerated herein, will be apparent to those skilled in the art from the foregoing description. Such modifications and variations are intended to fall within the scope of the appended claims. The present invention is to be limited only by the terms of the appended claims, along with the full scope of equivalents to which such claims are entitled.

The Examples set forth below are meant to be illustrative, and in no way limiting, of the scope of the present invention.

EXAMPLES

Materials and Methods:

MASCs: Rat MASCs (Wistar strain) are isolated and cultured as described in M. Dezawa et al., *Sciatic nerve regeneration in rats induced by transplantation of in vitro differentiated bone-marrow stromal cells.* Eur. J. Neurosci. 14, 1771-1776 (2001). As for human MASCs, commercially purchased MASCs (PT-2501, BioWhittaker. Walkersville, Md.) and MASCs obtained from healthy donors are used. Cells may be maintained in alpha-MEM (Sigma, M-4526) with 10% fetal bovine serum (FBS).

In the case of obtaining MASCs from healthy donors, an initial step is to obtain bone marrow aspirate from healthy donors using conventional aspiration techniques. The cell aspirate is then transferred into a 50 ml tube. 13 ml Histopaque is then carefully underlayed, using a 10 ml pipette. The tube is then centrifuged @ 2000 rpm for 20 minutes. Cells at the interphase are then harvested. PBS is then added (at least 3× the volume of the interphase) and the mixture centrifuged @ 1200 rpm. The cells are washed twice more with PBS. The cell pellet is then resuspended in DMEM+ 10% FCS, and the cells counted. 5×10^6 cells are replated per T-75 tissue culture flask, and incubated for 3 days. On day 4, the non-adherent cells are removed and the flask washed three times with medium. The adherent cells are allowed to grow in the flask. When the cells reach 20-30% confluence, the content of 2-3 flasks are pooled and re-plated in one T-75 flask. When the cells in this pooled reach confluence, the cells are trypsinized using 0.05% trypsin and 0.02% EDTA. The cells are then washed and counted. The cells are then resuspended in Sigma alpha MEM+10% FBS (M-4526). In experiments where lipofection is to be used, it is important to insure that the medium contains no l-glu. Glutamine is not added. The cells are expanded for 2-4 weeks and are frozen in early passages. Cell surface markers in rat and human MASCs are analyzed with fluorescence activated cell analysis (FACS). In an embodiment, the MASCs express CD29, and CD90, but are negative for CD34, CD31, CD45, CD11b/c, and von Willebrand Factor consistent with M. Pittenger et al., *Multilineage potential of adult human mesenchymal stem cells*. Science 284, 143-147 (1999); and J. Kohyama et al., *Brain from bone: efficient "meta-differentiation" of marrow stroma-derived mature osteoblasts to neurons with Noggin or a demethylating agent.* Differentiation 68, 235-244 (2001) (FIG. 1A). The same result is obtained by immunocytochemistry. Adipogenic, chondrogenic and osteogenic differentiation of both rat and human MASCs are confirmed according to the method described by M. Pittenger et al., *Multilineage potential of adult human mesenchymal stem cells*. Science 284, 143-147.

FACS analysis. Cells at a final concentration of 1×10 7/ml are incubated with 1 mg of a monoclonal antibody in phosphate buffered saline (PBS). Incubations may be performed in the presence of 10 mg of mouse immunoglobulin to prevent nonspecific antibody binding. In rat MASCs, mouse anti-CD34 (Santa Cruz Antibodies) and hamster anti-CD29 (PharMingen, San Diego, Calif.) may be labeled with FITC, and controls may be incubated either with FITC-labeled anti-mouse or hamster IgG. Mouse anti-CD54 and CD11b/c may be all purchased from PharMingen. Mouse anti-von Willebrand factor and other antibodies needed in the practice of this invention may be obtained commercially. Controls may include cells stained either with non-immune mouse serum. If these antibodies are conjugated to FITC, the cells may be subsequently incubated with 1 mg of FITC-conjugated anti-mouse IgG. In human MASCs, phycoerythrin labeled mouse anti-CD34, CD29, CD54, CD11b/c and von Willebrand factor may be used, and controls may include cells stained with phycoerythrin labeled anti-mouse IgG. Data may be acquired and analyzed on a FACScalibur with CellQuest software (Becton Dickinson, Franklin Lakes, N.J.).

Immunocytochemistry. The general procedure is described in M. Dezawa et al., *Sciatic nerve regeneration in rats induced by transplantation of in vitro differentiated bone-marrow stromal cells*. Eur. J. Neurosci. 14, 1771-1776 (2001). After the fixation of cells with 4% paraformaldehyde in phosphate-buffered saline (PBS), they are incubated with primary antibodies for overnight at 4 Deg. C. Antibodies to nestin may be purchased commercially from PharMingen. Cells may be then incubated with secondary antibodies to Alexa Fluor 488 or 546 conjugated anti-mouse IgG, IgM, or rabbit IgG (Molecular Probes, Eugene, Oreg.) for 1 hour at room temperature, and TOTO-3 iodide (Molecular Probes) counter staining may be performed. Inspections may be made under a confocal laser scanning microscope (Radians 2000, Bio-Rad, Hertfordshire, UK).

Example 1

Human MASCs (PT-2501, BioWhittaker, Walkersville, Md.) were allowed to grow in culture in alpha-MEM containing 10% FBS generally according to E. Sudbeck et al., *Structure-based design of specific inhibitors of Janus kinase 3 as apoptosis-inducing antileukemic agents*. Clin. Cancer Res. 5, 1569-1582 (1999). The MASCs were incubated with 40 ug/ml 4-(4'-hydroxyphenyl)amino-6,7-dimethoxyquinazoline (WHI-131, Calbiochem, San Diego, Calif.) for two days. The WHI-131 was washed off after 2 days.

Example 2

Human MASCs, prepared according to the Materials and Methods section, are allowed to grow in culture in alpha-MEM containing 10% FBS generally according to E. Sudbeck et al., *Structure-based design of specific inhibitors of Janus kinase 3 as apoptosis-inducing antileukemic agents*. Clin. Cancer Res. 5, 1569-1582 (1999). Once the culture has reached 90% confluence, several RNAs, designed using the BLOCK-iT™ RNAi Designer (Invitrogen) are incubated with the culture for a period of time sufficient to silence Sox9 expression, using BLOCK-iT™ protocols available from Invitrogen. Resulting CPCs are isolated from untransdifferentiated MASC's by sequential selection using magnetic beads coated with appropriate antibodies such as anti-EfnB2 (positive selection for CPCs), anti-CD90 (negative selection for CPCs), and anti-PDGF receptor beta (negative selection for CPCs). The antibodies and coated beads may be obtained from commercial suppliers. The cells in PBS are incubated with coated beads for 1 hr. @ room temperature. The cell-bound beads are removed using a magnet. The CPCs are washed free of the antibody and re-suspended in alpha-MEM containing 10% FBS and allowed to proliferate.

Example 3

Human MASCs, prepared according to the Materials and Methods section, are allowed to grow in culture in alpha-MEM containing 10% FBS generally according to E. Sudbeck et al., *Structure-based design of specific inhibitors of Janus kinase 3 as apoptosis-inducing antileukemic agents*. Clin. Cancer Res. 5, 1569-1582 (1999). Antisense oligomers to Hes 1 are generated according to techniques disclosed in any one of H. Moulton et al., *Peptide-assisted delivery of steric-blocking antisense oligomers*. Curr Opin Mol Ther. 2003 April;5(2):123-32; C. Stein et al., *Antisense oligonucleotides as therapeutic agents—is the bullet really magical?* Science. 1993 August 20;261(5124):1004-12; or C. Helene, *The anti-gene strategy: control of gene expression by triplex-forming-oligonucleotides*. Anticancer Drug Des. 1991 December;6(6):569-84. Once the MASC culture reaches 90% confluence, the Hes-1 antisense oligomers are incubated with the MASCs for a period sufficient to downregulate Hes-1 expression, according to techniques disclosed in any of the three references cited in this example. Resulting CPCs are isolated from untransdifferentiated MASC's by sequential selection using magnetic beads coated with appropriate antibodies such as anti-EfnB2 (positive selection for CPCs), anti-CD90 (negative selection for CPCs), and anti-PDGF receptor beta (negative selection for CPCs). The antibodies and coated beads may be obtained from commercial suppliers. The cells in PBS are incubated with coated beads for 1 hr. @ room temperature. The cell-bound beads are removed using a magnet. The CPCs are washed free of the antibody and re-suspended in alpha-MEM containing 10% FBS and allowed to proliferate.

Example 4

Wnt-1 expression plasmids are generated according to M. Sen et al., *Regulation of fibronectin and metalloproteinase expression by Wnt signaling in rheumatoid arthritis synoviocytes*. Arthritis Rheum. 2002 November;46(11):2867-77. Human MASCs, prepared according to the Materials and Methods section, are allowed to grow in culture in alpha-MEM containing 10% FBS generally according to E. Sudbeck et al., *Structure-based design of specific inhibitors of Janus kinase 3 as apoptosis-inducing antileukemic agents*. Clin. Cancer Res. 5, 1569-1582 (1999). Once the culture reaches 90% confluence, the MASCs are incubated with the Wnt-1 expression plasmids for two days at 37 deg C. and 5% CO2 using the Lipofectamine™ 2000 reagent and protocols available from Invitrogen. After the two days of incubation, the culture is selected for transfected cells using conventional selection techniques for a period of 10 days. Resulting CPCs are isolated from untransdifferentiated MASC's by sequential selection using magnetic beads coated with appropriate antibodies such as anti-EfnB2 (positive selection for CPCs), anti-CD90 (negative selection for CPCs), and anti-PDGF receptor beta (negative selection for CPCs). The antibodies and coated beads may be obtained from commercial suppliers. The cells in PBS are incubated with coated beads for 1 hr. @ room temperature. The cell-bound beads are removed using a magnet. The CPCs are washed free of the antibody and re-suspended in alpha-MEM containing 10% FBS and allowed to proliferate.

Example 5

The cells produced according to Example 1 were placed in Minimum Essential Medium Alpha Eagle Modification (M4526, Sigma Co.) containing 20% fetal bovine serum (14-501 F, Lot #61-1012, BioWhittaker Co.). 5 microM of forskolin (344273, Calbiochem, La Jolla, Calif.), 10 ng/ml of recombinant human basic fibroblast growth factor (100-18B, Peprotech EC, Ltd., London, UK) and 10 ng/ml of ciliary neurotrophic factor (557-NT, R&D Systems, Minneapolis, Minn.) were added. The culture was grown for 3 days, at which point cells that exhibit one or more characteristics of neurons were recognized, with the result of 29.46+/−3.0% of MAP-2ab-positive cells. MAP-2ab was analyzed for using Western blotting, with cell lysates prepared from incubated cells, and 50 ug of lysate proteins electrophoresed on 5% and 10% SDS-polyacrylamide gel. Antigens to MAP-2 (1:500, Chemicon) were detected using alkaline phosphatase.

Example 6

The cells that exhibit one or more characteristics of neurons of Example 5 are harvested, and grown to 90% confluence in culture in alpha-MEM containing 10% FBS generally according to E. Sudbeck et al., *Structure-based design of specific inhibitors of Janus kinase 3 as apoptosis-inducing antileukemic agents*. Clin. Cancer Res. 5, 1569-1582 (1999). Next, 5 mM of forskolin (344273, Calbiochem), 10 ng/ml of basic fibroblast growth factor (100-18B, Peprotech EC, Ltd.) and 50 ng/ml of ciliary neurotrophic factor (557-NT, R&D Systems) are added to the cell culture.

The cells are grown for ten days in the presence of the neurotrophic agents, and then are analyzed for the characteristic morphology of neural cells and for positive reaction for antibodies against MAP-2 (MAB364, Chemicon), neurofilament (814342, Boehringer Manheim) and nestin (BMS4353, Bioproducts)

PUBLICATIONS

Bishop, A. E., Buttery, L. D. & Polak, J. M. Embryonic stem cells (Review). J. Pathol. 197, 424-429 (2002).

Weissman, I. L. Stem cells: units of development, units of regeneration, and units in evolution (Review). Cell 100, 157-168 (2000).

Pittenger, M. F. et al. Multilineage potential of adult human mesenchymal stem cells. Science 284, 143-147 (1999).

Dezawa, M. et al. Sciatic nerve regeneration in rats induced by transplantation of in vitro differentiated bone-marrow stromal cells. Eur. J. Neurosci. 14, 1771-1776 (2001).

Jiang, Y. et al. Pluripotency of mesenchymal stem cells derived from adult marrow. Nature 418, 41-49 (2002).

Eglitis, M. A., Dawson, D., Park, K. W. & Mouradian, M. M. Targeting of marrow-derived astrocytes to the ischemic brain. Neuroreport 10, 1289-1292 (1999).

Kopen, G. C., Prockop, D. J. & Phinney, D. G. Marrow stromal cells migrate throughout forebrain and cerebellum, and they differentiate into astrocytes after injection into neonatal mouse brains. Proc. Natl. Acad. Sci. U S A 96, 10711-10716 (1999).

Terada, N. et al. Bone marrow cells adopt the phenotype of other cells by spontaneous cell fusion. Nature 416, 542-545 (2002).

Wagers, A. J., Sherwood, R. I., Christensen, J. L. & Weissman, I. L. Little evidence for developmental plasticity of adult hematopoietic stem cells. Science 297, 2256-2259 (2002).

Woodbury, D., Schwarz, E. J., Prockop, D. J. & Black, I. B. Adult rat and human bone marrow stromal cells differentiate into neurons. J. Neurosci. Res. 61, 364-370 (2000).

Kohyama, J. et al. Brain from bone: efficient "meta-differentiation" of marrow stroma-derived mature osteoblasts to neurons with Noggin or a demethylating agent. Differentiation 68, 235-244 (2001).

Sanchez-Ramos, J R. Neural cells derived from adult bone marrow and umbilical cord blood. J. Neurosci. Res. 69, 880-893 (2002).

Lundkvist, J. & Lendahl, U. Notch and the birth of glial cells (Review). Trends Neurosci. 24, 492-494 (2001).

Morrison, S. J. et al. Transient Notch activation initiates an irreversible switch from neurogenesis to gliogenesis by neural crest stem cells. Cell 101, 499-510 (2000).

Gaiano, N., Nye, J. S. & Fishell, G. Radial glial identity is promoted by Notch1 signaling in the murine forebrain. Neuron 26, 395-404 (2000).

Nye, J. S., Kopan, R. & Axel, R. An activated Notch regulates neurogenesis and myogenesis but not gliogenesis in mammalian cells. Development 120, 2421-2430 (1994).

Yamamoto, N. et al. Role of Deltex-1 as a transcriptional regulator downstream of the Notch receptor. J. Biol. Chem. 276, 45031-45040 (2001).

Shibata, T. et al. Glutamate transporter GLAST is expressed in the radial glia-astrocyte lineage of developing mouse spinal cord. J. Neurosci. 17, 9212-9219 (1997).

Yamasaki, M. et al. 3-Phosphoglycerate dehydrogenase, a key enzyme for l-serine biosynthesis, is preferentially expressed in the radial glia/astrocyte lineage and olfactory ensheathing glia in the mouse brain. Neurosci. 21, 7691-7704 (2001).

Gregg, C. T., Chojnacki, A. K. & Weiss, S. Radial glial cells as neuronal precursors: the next generation! J. Neurosci. Res. 69, 708-713 (2002).

Roy, N. S. et al. In vitro neurogenesis by progenitor cells isolated from the adult human hippocampus. Nat. Med. 6, 271-277 (2000).

Ip, N. Y. The neurotrophins and neuropoietic cytokines: two families of growth factors acting on neural and hematopoietic cells (Review). Ann. N. Y. Acad. Sci. 840, 97-106 (1998).

Grosse, G. et al. Expression of Kv1 potassium channels in mouse hippocampal primary cultures: development and activity-dependent regulation. J. Neurosci. 20, 1869-1882 (2000).

Morrison, S. J. Neuronal differentiation: proneural genes inhibit gliogenesis (Review). Curr. Biol. 11, R349-351 (2001).

Sun, Y. et al. Neurogenin promotes neurogenesis and inhibits glial differentiation by independent mechanisms. Cell 104, 365-376 (2001).

Ishibashi, M. et al. Persistent expression of helix-loop-helix factor HES-1 prevents mammalian neural differentiation in the central nervous system. EMBO J. 13, 1799-1805 (1994).

Furukawa, T. et al. rax, Hes1, and notch1 promote the formation of Muller glia by postnatal retinal progenitor cells. Neuron 26, 383-394 (2000).

Kahn, M. A. et al. Ciliary neurotrophic factor activates JAK/Stat signal transduction cascade and induces transcriptional expression of glial fibrillary acidic protein in glial cells. J. Neurochem. 68, 1413-1423 (1997).

Seidel, H. M., Lamb, P. & Rosen, J. Pharmaceutical intervention in the JAK/STAT signaling pathway (Review). Oncogene 19, 2645-2656 (2000).

Burdon, T., Smith, A. & Savatier, P. Signalling, cell cycle and pluripotency in embryonic stem cells. Trends Cell Biol. 12, 432-438 (2002).

Nakashima, K. et al. BMP2-mediated alteration in the developmental pathway of fetal mouse brain cells from neurogenesis to astrocytogenesis. Proc. Natl. Acad. Sci. U S A. 98, 5868-5873 (2001).

Stork, P. J. & Schmitt, J. M. Crosstalk between cAMP and MAP kinase signaling in the regulation of cell proliferation. Trends Cell Biol. 12, 258-266 (2002).

Neufeld, B. et al. Serine/Threonine kinases 3pK and MAPK-activated protein kinase 2 interact with the basic helix-loop-helix transcription factor E47 and repress its transcriptional activity. J. Biol. Chem. 275, 20239-20242 (2000).

Shimazaki, T., Shingo, T. & Weiss, S. The ciliary neurotrophic factor/leukemia inhibitory factor/gp130 receptor complex operates in the maintenance of mammalian forebrain neural stem cells. J. Neurosci. 21, 7642-7653 (2001).

Kurooka, H., Kuroda, K. & Honjo, T. Roles of the ankyrin repeats and C-terminal region of the mouse notch1 intracellular region. Nucleic Acids Res. 26, 5448-5455 (1998).

Franklin, J. L. et al. Autonomous and non-autonomous regulation of mammalian neurite development by Notch1 and Delta1. Curr. Biol. 9, 1448-1457 (1999).

Akerud, P. et al. Differential effects of glial cell line-derived neurotrophic factor and neurturin on developing and adult substantia nigra dopaminergic neurons. J. Neurochem. 73, 70-78 (1999)

Sakurada, K., Ohshima-Sakurada, M., Palmer, T. D. & Gage, F. H. Nurr1, an orphan nuclear receptor, is a transcriptional activator of endogenous tyrosine hydroxylase in neural progenitor cells derived from the adult brain. Development 126, 4017-4026 (1999).

Kim, J. H. et al. Dopamine neurons derived from embryonic stem cells function in an animal model of Parkinson's disease. Nature 418, 50-56 (2002).

Song, H. J., Stevens, C. F. & Gage, F. H. Neural stem cells from adult hippocampus develop essential properties of functional CNS neurons. Nat. Neurosci. 5, 438-445 (2002).

Weinmaster, G., Roberts, V. J. & Lemke, G. A homolog of Drosophila Notch expressed during mammalian development. Development 113, 199-205 (1991).

Peyton, M. et al. BETA3, a novel helix-loop-helix protein, can act as a negative regulator of BETA2 and MyoD-responsive genes. Mol. Cell Biol. 16, 626-33 (1996).

Rozovsky, I. et al. Estradiol (E2) enhances neurite outgrowth by repressing glial fibrillary acidic protein expression and reorganizing laminin. Endocrinology 143, 636-646 (2002).

Sudbeck, E. A. et al. Structure-based design of specific inhibitors of Janus kinase 3 as apoptosis-inducing antileukemic agents. Clin. Cancer Res. 5, 1569-1582 (1999).

Seta, Y., Toyono, T., Takeda, S. & Toyoshima, K. Expression of Mash1 in basal cells of rat circumvallate taste buds is dependent upon gustatory innervation. FEBS Lett. 444, 43-46 (1999).

Schwaiger, F. W. et al. Peripheral but not central axotomy induces changes in Janus kinases (JAK) and signal transducers and activators of transcription (STAT). Eur. J. Neurosci. 12, 1165-1176 (2000).

Kawasaki, H. et al. Induction of midbrain dopaminergic neurons from ES cells by stromal cell-derived inducing activity. Neuron 28, 31-40 (2000).

Tanaka, H. et al. Role of serotonergic neurons in L-DOPA-derived extracellular dopamine in the striatum of 6-OHDA-lesioned rats. Neuroreport 10, 631-634 (1999).

I claim:

1. A method for making a population of mammalian mitotic cells that express nestin and EfnB2, wherein the method comprises culturing mammalian marrow adherent stem cells (MASCs) in the presence of a Janus kinase (JAK) inhibitor and isolating the mitotic cells that express nestin and EfnB2; thereby providing a population of mammalian mitotic cells, in the absence of a JAK inhibitor, that express nestin and EfnB2.

2. The method of claim 1, wherein the mammalian MASCs are selected from the group consisting of human marrow adherent stem cells, rat marrow adherent stem cells, mouse marrow adherent stem cells, primate marrow adherent stem cells, pig marrow adherent stem cells, cow marrow adherent stem cells, and sheep marrow adherent stem cells.

3. The method of claim 2, wherein the mammalian MASCs are human MASCs.

4. The method of claim 1, wherein the JAK inhibitor is a synthetic small molecule organic compound.

5. The method of claim 4, wherein the small molecule JAK inhibitor is a dimethoxyquinazoline compound.

6. The method of claim 5, wherein the dimethoxyquinazoline compound is selected from the group consisting of 4-(phenyl)-amino-6,7-dimethoxyquinazoline; 4-(4'-hydroxyphenyl)-amino-6,7-dimethoxyquinazoline; 4-(3'- bromo-4'-hydroxylphenyl)-amino-6,7-dimethoxyquinazoline; and 4-(3',5'-dibromo-4'-hydroxylphenyl)-amino-6,7-dimethoxyquinazoline.

7. The method of claim 6, wherein the dimethoxyquinazoline compound is 4-(4'-hydroxyphenyl)-amino-6,7-dimethoxyquinazoline.

8. The method of claim 1, wherein the JAK inhibitor is a cAMP elevating agent.

9. The method of claim 8, wherein the cAMP elevating agent is selected from the group consisting of forskolin and 3-isobutyl-1-methylxanthine (IBMX).

10. The method of claim 1, wherein the JAK inhibitor is selected from the group consisting of 4,5-dimethoxy-2-nitrobenzoic acid and 4,5-dimethoxy-2-nitrobenzamide.

11. The method of claim 1, wherein the JAK inhibitor is a RNAi.

12. The method of claim 1, wherein the JAK inhibitor is an antisense oligonucleotide that downregulates JAK activity.

13. The method of claim 1, wherein the JAK inhibitor is a polypeptide.

14. The method of claim 13, wherein the culturing comprises transfection of the mammalian MASCs with a polynucleotide encoding the polypeptide.

15. The method of claim 1, wherein subsequent culture of the mammalian mitotic cells that express nestin and EfnB2; in the presence of forskolin, basic fibroblast growth factor and ciliary neurotrophic factor, and in the absence of the JAK inhibitor; generates a population comprising mammalian MAP-2-positive cells.

* * * * *

UNITED STATES PATENT AND TRADEMARK OFFICE
CERTIFICATE OF CORRECTION

PATENT NO. : 9,441,199 B2
APPLICATION NO. : 14/735005
DATED : September 13, 2016
INVENTOR(S) : Mari Dezawa It is certified that error appears in the above-identified patent and that said Letters Patent is hereby corrected as shown below:

In the Specification
1. In Column 1, Line 8, please replace "patent application" with --Patent Application--.
2. In Column 1, Line 10, please replace "patent application" with --Patent Application--.
3. In Column 1, Line 11, please replace "patent application" with --Patent Application--.
4. In Column 1, Line 47, please replace "*Stem cells: units of development, units of regeneration, and units in evolution (Review).*" with --Stem cells: units of development, units of regeneration, and units in evolution (Review).--.
5. In Column 3, Line 32, please replace "*Large-scale expansion of mammalian neural stem cells: a review.*" with --Large-scale expansion of mammalian neural stem cells: a review.--.
6. In Column 3, Line 59, please replace "*Large-scale expansion of mammalian neural stem cells: a review.*" with --Large-scale expansion of mammalian neural stem cells: a review.--.
7. In Column 4, Line 45, please replace "*Identification of mesenchymal stem/progenitor cells in human first trimester fetal blood,* liver, and bone marrow." with --Identification of mesenchymal stem/progenitor cells in human first trimester fetal blood, liver, and bone marrow.--.
8. In Column 4, Line 49, please replace "*Mesenchymal progenitor cells in human umbilical cord blood.*" with --Mesenchymal progenitor cells in human umbilical cord blood.--.
9. In Column 4, Line 53, please replace "*Induction of umbilical cord blood mesenchymal stem cells into neuron-like cells in vitro.*" with --Induction of umbilical cord blood mesenchymal stem cells into neuron-like cells in vitro.--.
10. In Column 5, Line 36, please insert an indent for a new paragraph at the beginning of "In an embodiment, glial...".
11. In Column 5, Line 50, please replace "*Id1, Id2, and Id3 gene expression in neural cells during development.*" with --Id1, Id2, and Id3 gene expression in neural cells during development.--.
12. In Column 5, Line 57, please replace "*Drosphila*" with --Drosophila--.
13. In Column 5, Line 59, please replace "*The potential to induce glial differentiation is conserved between Drosophila and mammalian glial cells missing genes.*" with --The potential to induce glial differentiation is conserved between Drosophila and mammalian glial cells missing genes.--.
14. In Column 5, Line 63, please replace "*GCMB, a second human homolog of the fly glide/gcm gene.*" with --GCMB, a second human homolog of the fly glide/gcm gene.--.

Signed and Sealed this
Thirtieth Day of July, 2019

Andrei Iancu
*Director of the United States Patent and Trademark Office*

CERTIFICATE OF CORRECTION (continued)
U.S. Pat. No. 9,441,199 B2

15. In Column 6, Line 6, please replace "*The Sox9 transcription factor determines glial fate choice in the developing spinal cord.*" with --The Sox9 transcription factor determines glial fate choice in the developing spinal cord.--.

16. In Column 6, Line 28, please replace "*Wnt-1 promotes neuronal differentiation and inhibits gliogenesis in P19 cells.*" with --Wnt-1 promotes neuronal differentiation and inhibits gliogenesis in P19 cells.--.

17. In Column 7, Line 5, please replace "*A stem cell molecular signature.*" with --A stem cell molecular signature.--.

18. In Column 7, Line 21, please replace "*Sciatic nerve regeneration in rats induced by transplantation of in vitro differentiated bone-marrow stromal cells.*" with --Sciatic nerve regeneration in rats induced by transplantation of in vitro differentiated bone-marrow stromal cells.--.

19. In Column 8, Line 22, please replace "*Intraarterial administration of marrow stromal cells in a rat model of traumatic brain injury.*" with --Intraarterial administration of marrow stromal cells in a rat model of traumatic brain injury.--.

20. In Column 8, Line 51, please replace "*Sciatic nerve regeneration in rats induced by transplantation of in vitro differentiated bone-marrow stromal cells.*" with --Sciatic nerve regeneration in rats induced by transplantation of in vitro differentiated bone-marrow stromal cells.--.

21. In Column 9, Line 15, please insert an indent for a new paragraph at the beginning of "Cell surface markers...".

22. In Column 9, Line 20, please replace "*Multilineage potential of adult human mesenchymal stem cells.*" with --Multilineage potential of adult human mesenchymal stem cells.--.

23. In Column 9, Line 22, please replace "*Brain from bone: efficient "meta-differentiation" of marrow stroma-derived mature osteoblasts to neurons with Noggin or a demethylating agent.*" with --Brain from bone: efficient "meta-differentiation" of marrow stroma-derived mature osteoblasts to neurons with Noggin or a demethylating agent.--.

24. In Column 9, Line 29, please replace "*Multilineage potential of adult human mesenchymal stem cells.*" with --Multilineage potential of adult human mesenchymal stem cells.--.

25. In Column 9, Line 32, please replace "FACS analysis" with --FACS analysis--.

26. In Column 9, Line 54, please replace "Immunocytochemistry." with --Immunocytochemistry.--.

27. In Column 9, Line 55, please replace "*Sciatic nerve regeneration in rats induced by transplantation of in vitro differentiated bone-marrow stromal cells.*" with --Sciatic nerve regeneration in rats induced by transplantation of in vitro differentiated bone-marrow stromal cells.--.

28. In Column 10, Line 9, please replace "*Structure-based design of specific inhibitors of Janus kinase 3 as apoptosis-inducing antileukemic agents.*" with --Structure-based design of specific inhibitors of Janus kinase 3 as apoptosis-inducing antileukemic agents.--.

29. In Column 10, Line 21, please replace "*Structure-based design of specific inhibitors of Janus kinase 3 as apoptosis-inducing antileukemic agents.*" with --Structure-based design of specific inhibitors of Janus kinase 3 as apoptosis-inducing antileukemic agents.--.

30. In Column 10, Line 45, please replace "*Structure-based design of specific inhibitors of Janus kinase 3 as apoptosis-inducing antileukemic agents.*" with --Structure-based design of specific inhibitors of Janus kinase 3 as apoptosis-inducing antileukemic agents.--.

31. In Column 10, Line 49, please replace "*Peptide-assisted delivery of steric-blocking antisense oligomers.*" with --Peptide-assisted delivery of steric-blocking antisense oligomers.--.

32. In Column 10, Line 51, please replace "*Antisense oligonucleotides as therapeutic agents- is the bullet really magical?*" with --Antisense oligonucleotides as therapeutic agents- is the bullet really magical?--.

CERTIFICATE OF CORRECTION (continued)
U.S. Pat. No. 9,441,199 B2

33. In Column 10, Line 54, please replace "*The anti-gene strategy: control of gene expression by triplex-forming- oligonucleotides.*" with --The anti-gene strategy: control of gene expression by triplex-forming-oligonucleotides.--.

34. In Column 11, Line 10, please replace "*Regulation of fibronectin and metalloproteinase expression by Wnt signaling in rheumatoid arthritis synoviocytes.*" with --Regulation of fibronectin and metalloproteinase expression by Wnt signaling in rheumatoid arthritis synoviocytes.--.

35. In Column 11, Line 16, please replace "*Structure-based design of specific inhibitors of Janus kinase 3 as apoptosis-inducing antileukemic agents.*" with --Structure-based design of specific inhibitors of Janus kinase 3 as apoptosis-inducing antileukemic agents.--.

36. In Column 11, Line 63, please replace "*Structure-based design of specific inhibitors of Janus kinase 3 as apoptosis-inducing antileukemic agents.*" with --Structure-based design of specific inhibitors of Janus kinase 3 as apoptosis-inducing antileukemic agents.--.